United States Patent
Homsma et al.

[11] Patent Number: 5,928,186
[45] Date of Patent: Jul. 27, 1999

[54] HIGH-FREQUENCY THROMBECTOMY CATHETER

[75] Inventors: Tjeerd Homsma, Roden; Alexander C. Boudewijn, Leek, both of Netherlands

[73] Assignee: Cordis Europa, N.V., Roden, Netherlands

[21] Appl. No.: 08/787,596

[22] Filed: Jan. 22, 1997

[30] Foreign Application Priority Data

Feb. 7, 1996 [NL] Netherlands ............................ 1002274

[51] Int. Cl.⁶ .................................................. A61B 17/20
[52] U.S. Cl. .................................................. 604/22
[58] Field of Search ............................ 604/22, 114, 30, 604/35, 36, 43, 118, 119, 246, 247

[56] References Cited

U.S. PATENT DOCUMENTS

| | | |
|---|---|---|
| 3,785,382 | 1/1974 | Schmidt-Kloiber et al. . |
| 4,808,153 | 2/1989 | Parisi ........................................ 604/22 |
| 5,344,395 | 9/1994 | Whalen et al. . |
| 5,380,273 | 1/1995 | Dubrul et al. ............................. 604/22 |
| 5,397,293 | 3/1995 | Alliger et al. . |
| 5,725,494 | 3/1998 | Brisken . |

FOREIGN PATENT DOCUMENTS

| | | | |
|---|---|---|---|
| 0 232 678 A2 | 12/1986 | European Pat. Off. ........ A61B 17/22 |
| 0 378 691 A1 | 7/1990 | European Pat. Off. ........ A61B 17/36 |
| 38 12841 A1 | 2/1989 | Germany ........................ A61B 17/22 |

*Primary Examiner*—John D. Yasko
*Assistant Examiner*—Manuel Mendez
*Attorney, Agent, or Firm*—Paul A. Coletti

[57] ABSTRACT

This invention related to a catheter comprising a tube-like basic body with a proximal and a distal end and a high-frequency generator associated with the catheter used for the purpose of generating high-frequency mechanical vibrations at the distal end of the catheter. The catheter comprises a lumen to be filled with liquid which is connected at the proximal end to an area inside of which a high-frequency movable member of the high-frequency generator is located and wherein at the distal end of the catheter a guide have been arranged for deflecting high frequency longitudinal waves traveling through the liquid inside the lumen in a lateral direction.

4 Claims, 2 Drawing Sheets

HIGH-FREQUENCY THROMBECTOMY CATHETER

FIELD OF THE INVENTION

The invention relates to a catheter used to remove thrombi from the blood vessels of a patient.

SUMMARY OF THE INVENTION

The catheter according to the invention comprises a tube-like basic body with a proximal and a distal end and a high-frequency generator to be used together with the catheter for the purpose of generating high-frequency mechanical vibrations at the distal end of the catheter.

The high-frequency mechanical vibrations generated by the high-frequency generator produce high-frequency longitudinal waves in the blood. These waves are absorbed by the thrombi, causing them to dissipate into the bloodstream. Or, the particles of thrombi thus formed can be removed by means of a mechanism such as a suction catheter.

A very suitable embodiment of the catheter according to the invention is characterized in FIG. 3. The lumen is filled with a saline-solution or blood, so that the mechanical vibrations generated by the high-frequency generator are propagated in the form of longitudinal waves toward the catheter distal end. The conducting means ensure that the high-frequency waves are aimed exclusively at the thrombi, in order to fragment them.

The cone-shaped mirror ensures that waves being propagated in the longitudinal direction of the catheter are deflected transversely at the distal end in order to be able to act on thrombi or other detritus attached to the walls of the blood vessel.

With the measures as set out in the invention, at the distal end of the catheter a uniform distribution of high-frequency energy is effected allowing thrombii in all radial directions to be dissipated.

Of course, the high-frequency mechanical vibrations are desirably generated in the immediate vicinity of the location where they are to be utilized.

At a suitable location the electrical excitation element is additionally a piezo-electric element. Thus, the required frequencies useful for thrombus fragmentation can be generated with sufficient power but using an element of limited size.

A very suitable further development of the catheter according to the invention is characterized herein. The fragmented thrombi can be removed from the body of the patient directly via a suction inlet contained in the catheter through the discharge lumen of the catheter.

To adjust the "shock" waves to the diameter of the blood vessel, the distance to the wall of the blood vessel and the size and condition of the thrombus to be fragmented the frequency of the wave is set by means of a frequency-adjusting-element contained in the catheter in such a way that maximal absorption of energy inside the thrombus is realized.

DESCRIPTION OF THE DRAWINGS

The invention will be explained in greater detail in the following description with reference to the attached drawings.

DETAILED DESCRIPTION OF THE INVENTION

Figure 1:
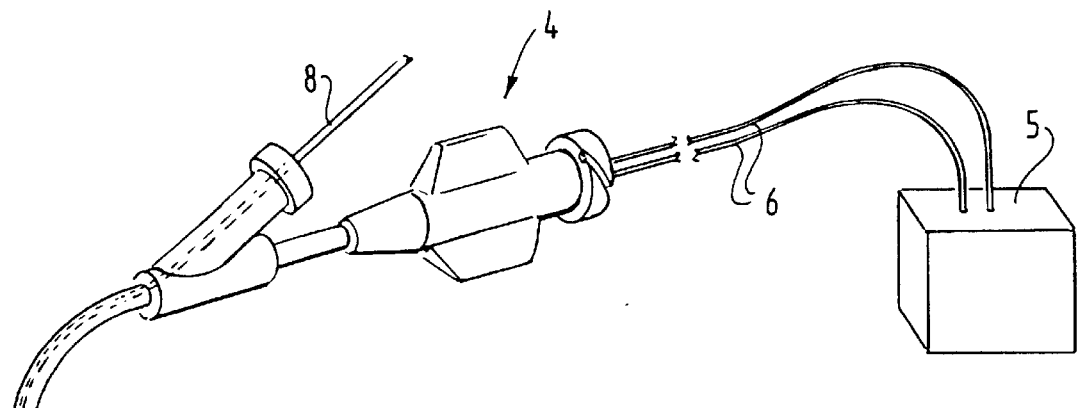
FIG. 1 shows schematically a catheter according to the invention.
Figure 1:
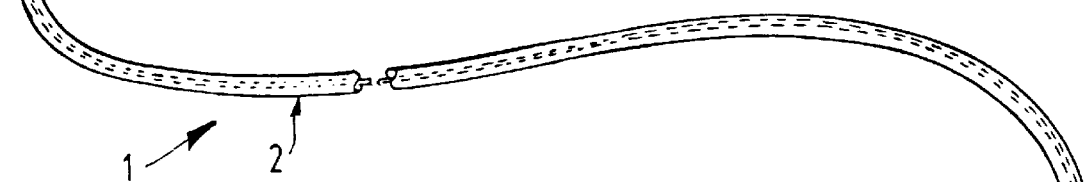

The catheter 1 illustrated in FIG. 1 comprises a tube-like basic body 2 with a distal end 3 and a proximal end 4. When in use the catheter 1 is introduced into a patient with the distal end. For this purpose a guide wire 8 can be used. The catheter 1 is passed with a lumen over the guide wire 8, until the distal end 3 has reached the desired position.

A high-frequency generator 5 is used together with the catheter 1. With the embodiment shown in FIG. 1, this high-frequency generator 5 is a substantially independent unit which can propagate high-frequency mechanical vibrations by means of lines 6 to the distal end 3 of the catheter 1. For this purpose there is a lumen inside the basic body 2 of the catheter 1 which is filled with a liquid when the catheter is used, which may be for instance a saline solution but also blood of the patient. With this embodiment the lines 6 may be tube-like lines, whereby a channel of these lines 6 is connected with the lumen referred to. The liquid is in that case also present in the lines 6.

The high-frequency generator 5 comprises a high-frequency movable member which is connected to the liquid inside the lines 6 and the above mentioned lumen of the basic body 2. This high-frequency movable member generates high-frequency longitudinal waves which are propagated through the liquid inside the lumen and through a window 7 at the distal end 3 of the catheter 1. These high-frequency longitudinal waves act on thrombi located at the distal end 3. These thrombi absorb the vibration-energy as a result of which they disintegrate. The thrombi thus fragmented can be removed by means of a suction catheter for instance.

Figure 2:
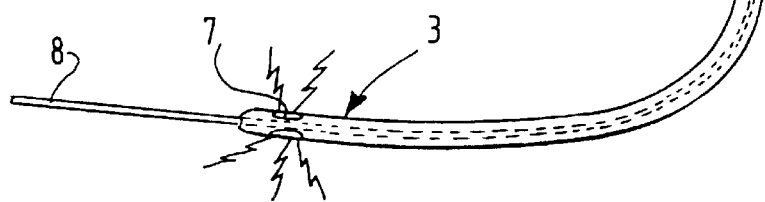
FIG. 2 shows the distal end-section of a preferred embodiment of the catheter according to the invention.
Figure 2:
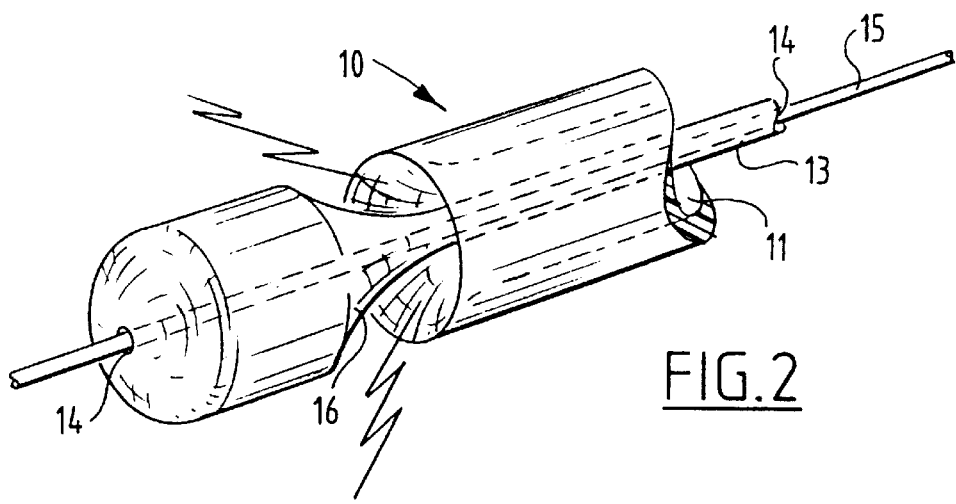

Apart from the end-section illustrated in FIG. 2, the catheter 10 as shown in FIG. 2 corresponds to the catheter 1 of FIG. 1. The high-frequency longitudinal waves are propagated through the lumen 11. Guiding means have been arranged at the distal end in the shape of a substantially cone-shaped mirror 16 diverging in the distal direction. The latter ensures that the high-frequency waves are deflected in a lateral direction, so that thrombi located at the side of the distal end 10 can be acted on.

With the example of an embodiment shown, the mirror 16 has been connected with an inner tube-like element 13 of the catheter which extends through the lumen 11. At the distal end this inner tube-like element has been connected with the outer tube-like element in a manner not described here, so that a fixed coaxial position of the inner tube-like element 13 inside the lumen 11 is obtained.

A lumen 14 extends through the inner tube-like element which is associated with a guide wire 15.

Figure 3:
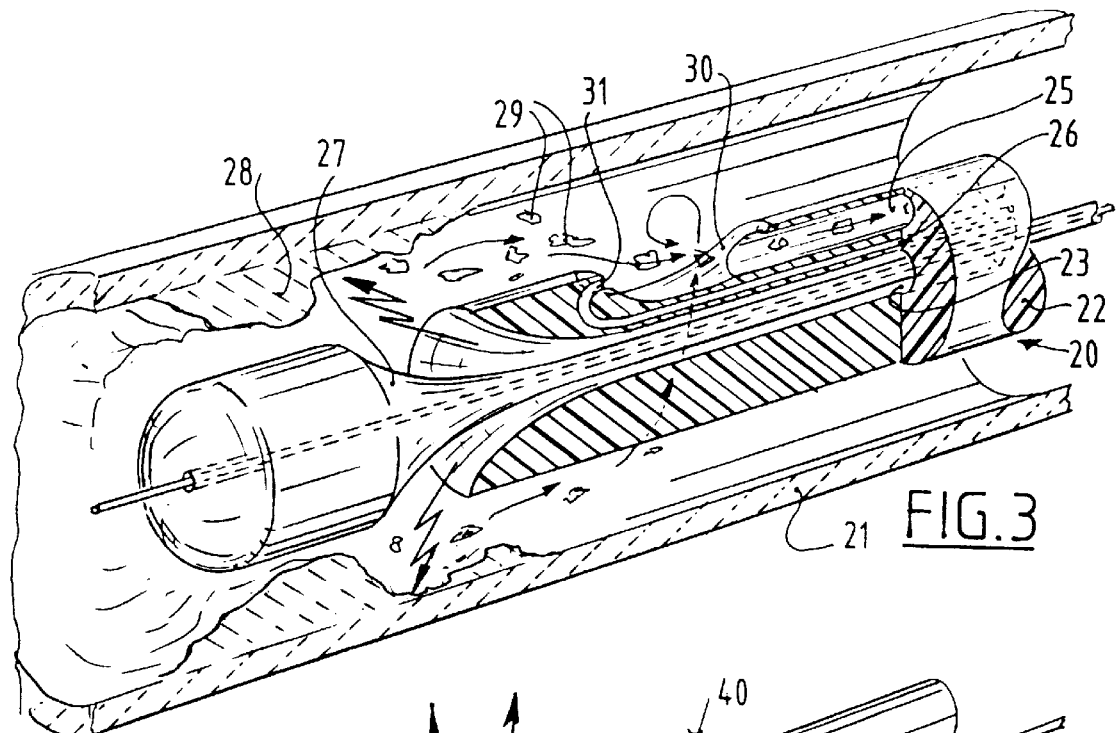
FIG. 3 illustrates a further developed embodiment of the catheter according to the invention in a position of use.

With the catheter 20 of FIG. 3 the high-frequency energy is also supplied via a central lumen 23 inside the basic body 22. The high-frequency waves are also in this case deflected in a lateral direction by a cone-shaped mirror 27, so that they can act on thrombi 28 or other deposits on the wall of a blood vessel 21 shown in FIG. 3.

Due to the action of the high-frequency waves, which may be of a continuous or pulsatory nature, the deposit 28 is fragmented. The catheter 20 has been provided with a discharge lumen 25 through which the fragments 29, which have come off the deposit 28, can be removed. For this purpose the catheter 20 has additionally been provided with a pressure lumen 26 through which liquid under high pressure can be supplied. The pressure lumen 26 opens into a jet nozzle 31 which directs a jet, past the suction inlet 30 in the discharge lumen 25, towards the inside. Because of this, due to ejector action, suction will be created in the suction inlet 30 as a result of which the loosened fragments 29 will be sucked in. Because of the actin of the jet produced by the jet nozzle 31, these fragments 29 are additionally reduced further in size so that they can be removed easily via the discharge lumen 25.

Figure 4:
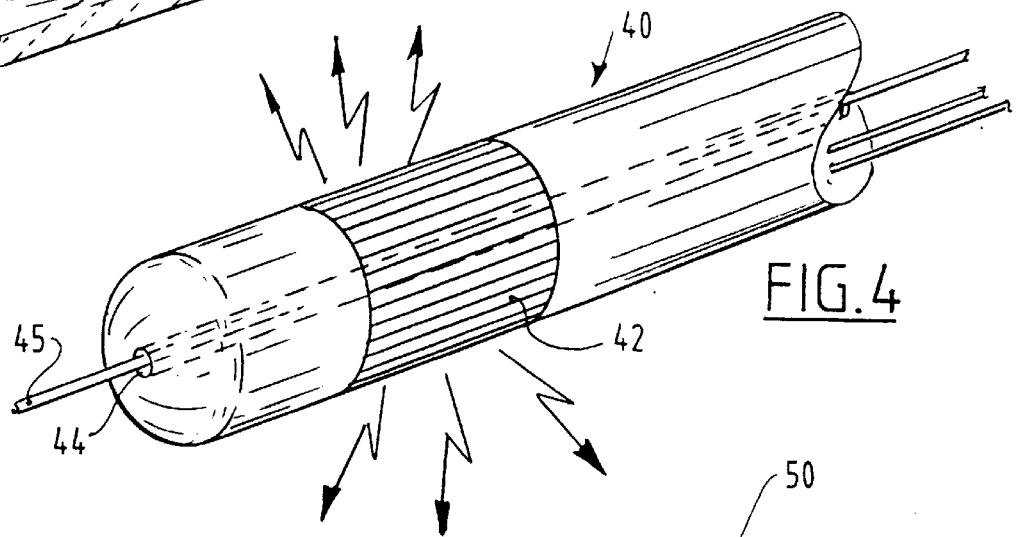
FIG. 4 shows an end-section of yet another embodiment.
Figure 5:
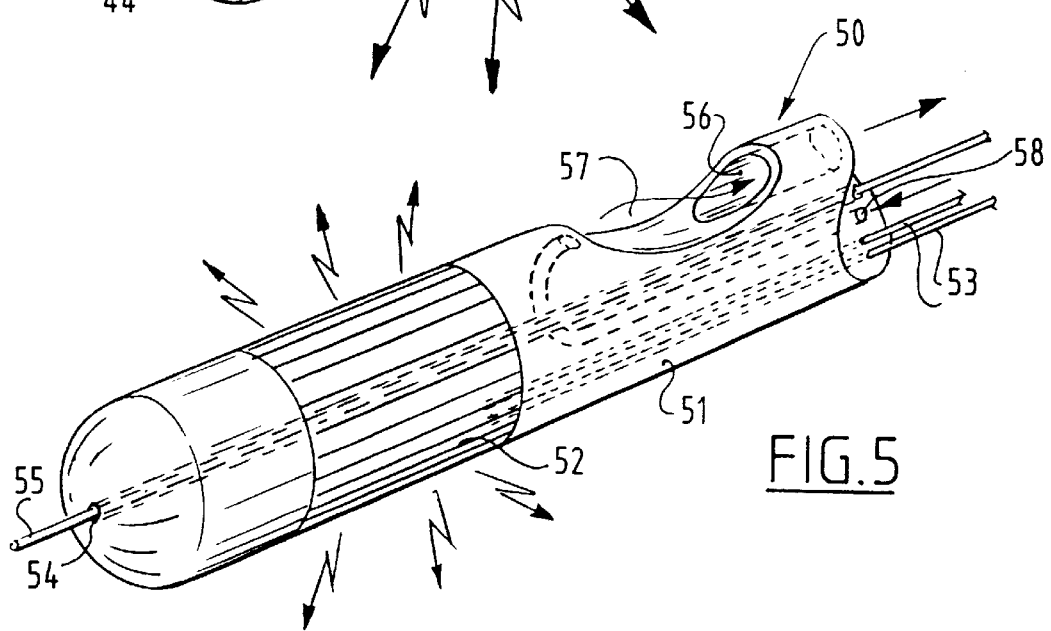
FIG. 5 shows a view substantially corresponding to FIG. 4 of a further developed embodiment of the catheter according to the invention.

The catheters 40 and 50 as shown in the FIGS. 4 and 5 respectively, comprise an integrated high-frequency generator instead of an external high-frequency generator. The high-frequency generator 42 of the catheter 40 is a piezo-electric element which is excited by means of electrical excitation lines 43 which extend from the proximal end through the basic body 41 to the high-frequency generator 42. By means of suitable excitation via the lines 43 the high-frequency generator 42 will start to vibrate mechanically as a result of which high-frequency waves are formed which are immediately passed on to the surrounding liquid, in particular blood. The blood will transmit the high-frequency waves to the thrombi to be fragmented.

As has been illustrated with the catheter 40, a central lumen 44 has been arranged which is associated with a guide wire 45.

The catheter 50 of FIG. 5 has also been provided with a high-frequency generator 52 integrated in the distal end of the catheter, comprising preferably a piezo-electric element. The excitation lines 53 for the high-frequency generator 52 extend through the basic body 51.

Inside the basic body 51 a suction lumen 56 has been arranged as well, which is accessible via an opening 57 in the wall of the basic body 51. Via a pressure line 58 liquid under high pressure is supplied which directs, in a manner analogous to the one described in relation to FIG. 3, a liquid jet past the opening 57 towards the suction lumen 56 in order to suck fragmented thrombi et cetera through the opening 57 and discharge them via the lumen 56. The catheter 50 is advanced in the manner described above to the intended position inside the body of the patient by means of a guide wire 55 extending through a lumen 54.

We claim:

1. Catheter comprising:

a tube-like catheter body with a proximal end and a distal end; and a high-frequency generator associated with the catheter used for the purpose of generating high-frequency mechanical vibrations at the distal end of the catheter, said generator containing a readily manipulable projecting member; and said catheter comprising a lumen, said catheter connected at its proximal end to an area inside of which at least a portion of said high-frequency generator can be inserted and located; and wherein guiding means are arranged said guiding means arranged at the distal end of the catheter, for deflecting in a lateral direction high-frequency longitudinal waves generated by said generator;

a suction inlet connected within a discharge lumen in the catheter body; and a pressure lumen connected to a jet nozzle directed in a proximal direction past said suction inlet; said pressure lumen for generating suction by means of pressure differential within said lumen.

2. Catheter as claimed in claim 1, wherein the high-frequency generator comprises an element excitable by means of electrical vibrations at its distal end and electrical lines extend from the proximal end of the catheter, through said tube-like body, to the element.

3. Catheter as claimed in claim 2, wherein the excitable element is a piezo-electric element.

4. Catheter as claimed in claim 1, wherein the high-frequency generator further comprises a frequency-adjusting-element.

\* \* \* \* \*